US008449183B2

(12) United States Patent
Seimiya

(10) Patent No.: US 8,449,183 B2
(45) Date of Patent: May 28, 2013

(54) X-RAY TUBE HOLDING DEVICE

(75) Inventor: Masao Seimiya, Tokyo (JP)

(73) Assignee: Kabushiki Kaisha Oobayashi Seisakusyo, Tokyo (JP)

( * ) Notice: Subject to any disclaimer, the term of this patent is extended or adjusted under 35 U.S.C. 154(b) by 350 days.

(21) Appl. No.: 12/733,939

(22) PCT Filed: Aug. 1, 2008

(86) PCT No.: PCT/JP2008/063844
§ 371 (c)(1),
(2), (4) Date: Aug. 11, 2010

(87) PCT Pub. No.: WO2009/136452
PCT Pub. Date: Nov. 12, 2009

(65) Prior Publication Data
US 2010/0310052 A1    Dec. 9, 2010

(30) Foreign Application Priority Data

May 9, 2008    (JP) .................................. 2008-123607

(51) Int. Cl.
*H05G 1/02*    (2006.01)
(52) U.S. Cl.
USPC ........................... 378/197; 378/196; 378/198

(58) Field of Classification Search
USPC .................................................. 378/195–198
See application file for complete search history.

(56) References Cited

U.S. PATENT DOCUMENTS

| | | | | |
|---|---|---|---|---|
| 4,435,830 A | * | 3/1984 | Suzuki et al. .................. | 378/197 |
| 4,805,202 A | * | 2/1989 | Deucher et al. ............... | 378/209 |
| 5,148,467 A | * | 9/1992 | Sato et al. ...................... | 378/197 |
| 5,550,891 A | * | 8/1996 | Burbury et al. ............... | 378/197 |
| 5,870,450 A | * | 2/1999 | Khutoryansky et al. ....... | 378/197 |
| 6,155,713 A | * | 12/2000 | Watanabe ...................... | 378/197 |
| 7,641,391 B2 | * | 1/2010 | Schwieker .................... | 378/197 |
| 7,832,927 B2 | * | 11/2010 | Dyreby et al. ................. | 378/197 |
| 2008/0069308 A1 | * | 3/2008 | Chapman ....................... | 378/197 |
| 2010/0310052 A1 | * | 12/2010 | Seimiya ........................ | 378/197 |

FOREIGN PATENT DOCUMENTS

| JP | 2005021470 | 1/2005 |
|---|---|---|
| JP | 2005065942 | 3/2005 |
| JP | 200634727 | 2/2006 |
| JP | 2008061944 | 3/2008 |

* cited by examiner

*Primary Examiner* — Thomas R Artman
(74) *Attorney, Agent, or Firm* — Jacobson Holman PLLC

(57) ABSTRACT

An operator who holds an operation handle and visually confirms a display body can accurately grasp imaging relevant information displayed in the display body irrespective of a posture of the X-ray tube.

5 Claims, 12 Drawing Sheets

Fig.7
(a)
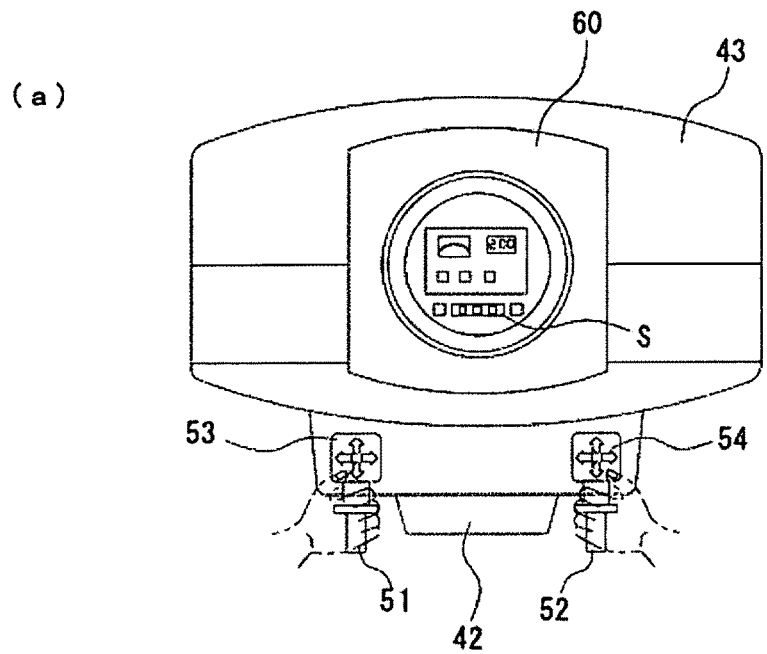
(b)
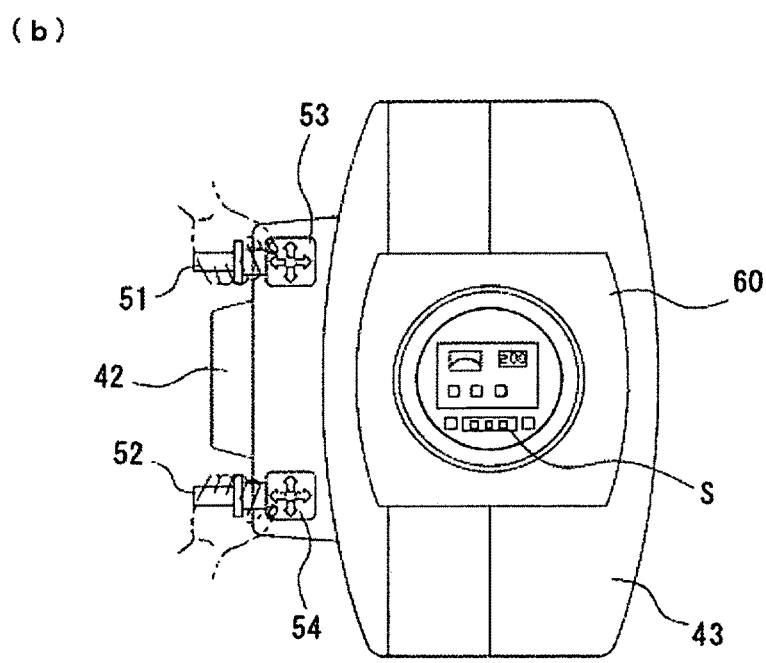

Fig.10
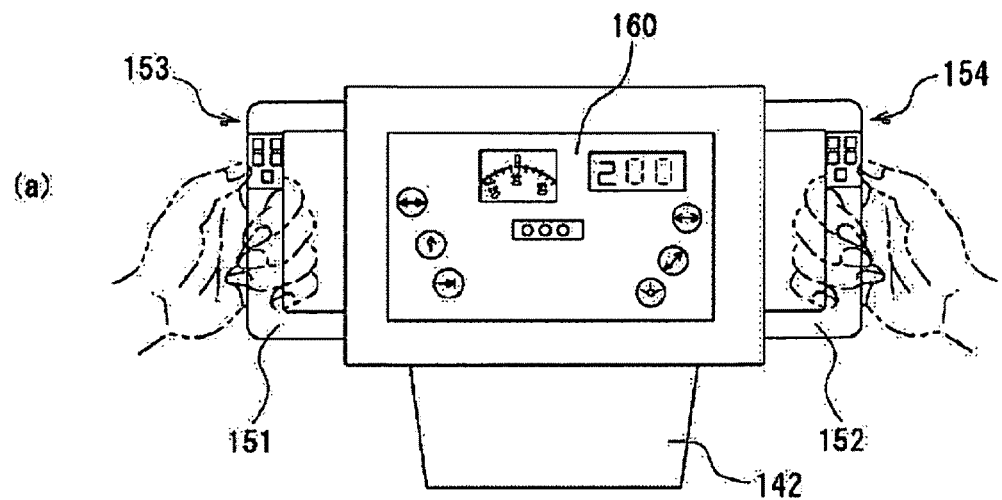
(a)
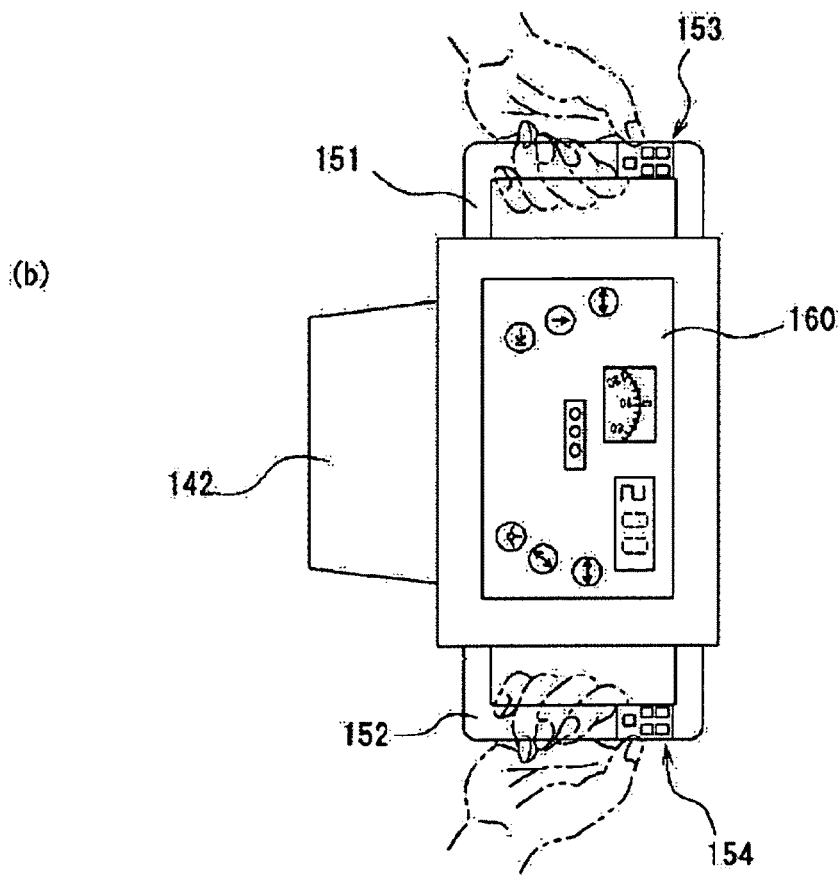
(b)

X-RAY TUBE HOLDING DEVICE

This is a national stage of PCT/JP08/063844 filed Aug. 1, 2008 and published in Japanese, which has a priority of Japanese no. 2008-123607 filed May 9, 2008, hereby incorporated by reference.

TECHNICAL FIELD

The present invention relates to an X-ray tube holding apparatus that holds an X-ray tube that irradiates an imaging subject such as a human body or a domestic animal with an X-ray to perform imaging.

BACKGROUND ART

As a conventional X-ray tube holding apparatus, there is, e.g., a ceiling hung type X-ray tube holding apparatus disclosed in Patent Document 1 or a floor traveling type X-ray imaging apparatus disclosed in Patent Document 2. These apparatuses will now be described with reference to FIGS. 8 to 12. FIG. 8 is a perspective view showing a configuration of a conventional ceiling hung type X-ray tube holding apparatus. FIG. 9(a) is a perspective view showing a state that the conventional X-ray tube holding apparatus depicted in FIG. 8 and an upright photography platform 170 are utilized to perform imaging, and FIG. 9(b) is a perspective view showing a state that the conventional X-ray tube holding apparatus depicted in FIG. 8 and a horizontal photography platform 175 are utilized to perform imaging. FIG. 10(a) is a front view showing arrangement of a display body 160 and an imaging unit 142 in an initial state in the conventional X-ray tube holding apparatus depicted in FIG. 8, and FIG. 10(b) is a front view showing arrangement when the display body 160 and the imaging unit 142 are swiveled 90 degrees with respect to the initial state in the conventional X-ray tube holding apparatus depicted in FIG. 8. FIG. 11 is a side view showing a configuration of a conventional floor traveling type X-ray photography apparatus. FIG. 12 is a front view showing the configuration of the conventional floor traveling type X-ray photography apparatus.

A ceiling hung type X-ray tube holding apparatus depicted in FIGS. 8 to 10 includes: a vertically extensible column support 132 (a vertical shaft) that is hung by a hanging platform 131 (a mount) from a fixed rail 122 and a moving rail 123 provided in X and Y directions of a ceiling; an X-ray tube apparatus 140; an operation panel 150 having operation switches 153 and 154 and operation handles 151 and 152 provided thereon; an attachment block 133 (a base unit) that is configured to rotatably attach the X-ray tube apparatus 140 and the operation panel 150 to the column support 132; and a display body 160 that displays imaging relevant information. The fixed rail 122 is fixed on the ceiling by fixtures 121, and the column support 132 is disposed to the moving rail 123 by the hanging platform 131. An X-ray is emitted from an imaging unit 142 toward the lower side in FIG. 10(a).

In this X-ray tube holding apparatus, when the operation switches 153 and 154 on the operation handles 151 and 152 are operated, the X-ray tube apparatus 140, the operation panel 150, and the display unit 160 can swivel on a horizontal axis 133c extending from the attachment block 133 (the base unit) in a θ2 direction in an integrated manner. Further, when the operation switches 153 and 154 on the operation handles 151 and 152 are operated, the attachment block 133 (the base unit) can swivel on a central axis of the column support 132 in a θ1 direction together with the X-ray tube apparatus 140, the operation panel 150, and the display body 160. Further, the attachment block 133 (the base unit) elongates and contracts the column support 132 with respect to the hanging platform 131 to move up and down its height in a Z direction without restraint by operating the operation switches 153 and 154, thereby enabling adjustment of a height direction of the X-ray tube apparatus 140 with respect to the ceiling. Furthermore, the entire X-ray tube apparatus 140 can operate the moving rail 123 to move in an X direction with respect to the fixed rail 122 and operate the hanging platform 131 (the mount) to move in a Y direction with respect to the moving rail 123 by operating the operation switches 153 and 154.

Therefore, the X-ray tube apparatus 140 can be translated to an arbitrary position in an XY direction with respect to the ceiling in a photography room, and it can be directed to an arbitrary height position and an arbitrary direction so that a photography subject (FIG. 9(a)) in front of the upright photography platform 170 can be, for example, photographed from the front side or from above of the photography subject on the horizontal photography platform 175. At this time, an operator (e.g., an X-ray operator) stands on a front surface side of the display body 160 and operates the operation switches 153 and 154 while visually confirming a screen of the display body 160 so that the imaging unit 142 can face an arbitrary direction with respect to the photography subject. Moreover, the operator changes over the operation switches 153 and 154 to a manual mode and manually performs translation of the X-ray tube apparatus 140 in the XY direction with respect to the ceiling, elevating movement in the Z direction, swiveling in the θ1 direction, and swiveling in the θ2 direction, whereby a position of the imaging unit 142 with respect to the photography subject can be finely adjusted. Additionally, the operator can come into contact with a touch switch displayed on the screen of the display body 160 to direct the X-ray tube 142 to an arbitrary direction or the photography subject.

On the other hand, the floor traveling type X-ray photography apparatus depicted in FIGS. 11 and 12 includes: a carriage 221 (a mount) that can translate in the XY direction with respect to a floor surface of the photography room; a column support 222 (a vertical shaft) held in front of the carriage 221 so as to allow its swiveling motion; an X-ray tube holding mechanism 230 having one end held by the column support 222 so as to allow its movement in a height direction; an X-ray tube 242 held at the other end of the X-ray tube holding mechanism 5; an operation panel 250 having operation switches 253 and 254 and operation handles 251 and 252 provided thereon, and a display body 260 that displays imaging relevant information. An X-ray is emitted from the X-ray tube 242 toward the lower side in each of FIGS. 11 and 12.

In this X-ray photography apparatus, when the operation switches 253 and 254 on the operation handles 251 and 252 are operated, the X-ray tube 242, the operation panel 250, and the display body 260 can swivel on a horizontal axis 230c extending from the X-ray tube holding mechanism 230 in a θ2 direction in an integrated manner. Moreover, when the operation switches 253 and 254 on the operation handles 251 and 252 are operated, the X-ray tube holding mechanism 230 can swivel on the central axis of the column support 222 in a θ1 direction together with the X-ray tube 242, the operation panel 250, and the display body 260, and can move up and down in the Z direction with respect to the column support 222. Further, the operator moves forward and backward the carriage 221 (the mount) with respect to the floor surface of the photography room to translate the entire X-ray photography apparatus in the XY direction. That is, the operator stands on the front surface side of the display body 260 and operates the operation switches 253 and 254 while visually confirming a screen of the display body 260 to direct the X-ray tube 242 in an arbitrary direction for the photography subject. Furthermore, the operator changes over the operation switches 253 and 254 to a manual mode to manually carry out elevating movement of the X-ray tube 242 in the Z direction, swiveling in the θ1 direction, and swiveling in the θ2 direction, whereby a position of the X-ray tube 242 with respect to the photography subject can be finely adjusted. Moreover, the operator can come into contact with a touch switch displayed on the screen of the display body 260 to direct the X-ray tube 242 to an arbitrary direction for the photography subject.

In this manner, the X-ray tube 242 can be directed to an arbitrary direction, thereby effecting photography from above the photography subject on the horizontal photography platform 275.

In conventional X-ray tube holding apparatuses including the ceiling hung type X-ray tube holding apparatus and the floor traveling type X-ray photography apparatus, when the X-ray tube is swiveled to perform photography, for example, as represented as transition from FIG. 10(a) to (b), the display unit integrated with the X-ray tube is also swiveled, whereby it is difficult for an operator to appropriately and rapidly grasp imaging relevant information displayed in the display unit. Specifically, in the example depicted in FIG. 10, when digital number indication is inclined 90 degrees, for example, a number "9" may be possibly erroneously recognized as "6". Further, in regard to an analog meter, an operator may get a different sensation. Therefore, the operator may possibly erroneously operate a direction of an operation button. In particular, since the operator stands on the front surface side of the display body and operates the operation switches while visually recognizing imaging relevant information on the display body, the possibility that the operator has his/her attention caught by display contents to erroneously operate the operation switches or that the operator has his/her attention caught by the operation switches to erroneously recognize display contents has been pointed out. Furthermore, when the operator changes over the operation switches to the manual mode to manually carry out elevating movement of the X-ray tube in the Z direction, swiveling in the θ1 direction, or swiveling in the θ2 direction, since a moving resistance of the entire X-ray tube is 1 to 2 kg, development of an apparatus that does not cause an erroneous operation in such an operation environment is expected.

As means for solving such a problem, in the X-ray tube holding apparatus described in Patent Document 1, two types of states where the operation switches are inclined at 0 degree and 90 degrees are prepared. Moreover, an X-ray tube holding apparatus described in Patent Document 3 includes a sensor that detects inclination of a display body and has software that can switch a screen in a state that display of the display body is inclined 90 degrees from 0 degree to the same state as 0 degree installed therein.

Patent Document 1: Japanese Patent Application Laid-open 2005-21470

Patent Document 2: Japanese Patent Application Laid-open No. 2008-61944

Patent Document 3: Japanese Patent Application Laid-open No. 2005-65942

DISCLOSURE OF INVENTION

Problem to be Solved by the Invention

However, including he sensor or the software leads to an increase in manufacturing cost of the X-ray tube holding apparatus. Additionally, even in case of changing display contents of a display unit of the display body or the operation switches at the time of swiveling, since arrangement or a size of display information in the display unit, arrangement of the operation switches, and others differ depending on an initial state and a state after swiveling, an operator cannot rapidly recognize displayed information, and he/she cannot immediately select an operation switch in some cases. Further, in the X-ray tube holding apparatus disclosed in Patent Document 3, display of imaging relevant information in the display body has two display versions that are switched between a 0-degree state and a 90-degree inclined state based on detection of an angle by the sensor, and hence an inconvenience that the operator may erroneously recognize display contents in an intermediate state that the display body is inclined at, e.g., approximately 45 degrees has been pointed out.

Therefore, according to the present invention, in an X-ray tube holding apparatus that includes: a vertical shaft that is hung from a ceiling or can travel on a floor surface by using casters and is arranged in a vertical direction with respect to the mount; a base unit that can swivel on an axial line of the vertical shaft and can be moved up and down; an X-ray tube which is extended from the base unit side toward a distal end side, axially supported to enable its swiveling motion around a swiveling shaft along a horizontal direction and includes an imaging unit which emits an X-ray toward a photography subject; and a display body which is disposed on the farther end side of the X-ray tube with respect to the base unit, provided on the distal end side of the X-ray tube, can be visually recognized by an operator when he/she faces it, and displays imaging relevant information, the operator who is on the distal end side of the X-ray tube with respect to the base unit being capable of swiveling the X-ray tube with respect to at least the base unit, translating the same with respect to the ceiling or the floor surface, moving up and down the same with respect to the ceiling or the floor surface, or swiveling the same on an axial line of the vertical shaft, the X-ray tube holding apparatus being configured to be translated in an X direction and a Y direction in a photography room, moved up and down in the vertical direction (a Z direction) by an elevating shaft with respect to a ceiling surface, and allow the X-ray tube to swivel on an axis along a direction vertical to the elevating shaft, an object of the present invention is to enable the operator who holds operation handles and visually confirms the display body to appropriately grasp imaging relevant information displayed in the display body irrespective of a posture of the X-ray tube. Specifically, an object of the present invention is to avoid erroneous recognition of the imaging relevant information, i.e., erroneous operations of the X-ray tube holding apparatus. Further, it is also an object of the present invention to improve operability of the X-ray tube holding apparatus to enable rapid and accurate photography.

Means for Solving Problem

To achieve the objects, according to the present invention, there is provided an X-ray tube holding apparatus comprising: a mount configured to be translated with respect to a ceiling or a floor surface; a vertical shaft arranged in a vertical direction with respect to the mount; a base unit configured to swivel on an axial line of the vertical shaft and move up and down; an X-ray tube that is provided on a distal end side in an irradiating direction with the base unit at the center, extends from the base unit side toward a distal end side, is axially supported to allow its swiveling motion on a swiveling shaft along a horizontal direction, and includes an imaging unit that applies an X-ray toward a photography subject; and a display body that is disposed to the distal end side distanced from the X-ray tube with respect to the base unit, provided on the distal end side of the X-ray tube, enables visual recognition when facing an operator who is directed to the base unit side, and displays imaging relevant information, the X-ray tube being configured to be swiveled with respect to at least the base unit, translated with respect to the ceiling or the floor surface, moved up and down with respect to the ceiling or the floor surface, or swiveled on the axial line of the vertical shaft by the operator who is on the distal end side of the X-ray tube for the base unit, wherein the X-ray tube holding apparatus comprises a coupling body that is axially supported on the swiveling shaft between the base unit and the display body, arranged between the base unit and the display body so as to bypass the X-ray tube arranged on the axial line of the swiveling shaft between the base unit and the display body, and enables coupling the base unit with the display body so as to maintain a posture of the display body even in a state that the display body is coupled with the base unit and the X-ray tube is swiveled on the swiveling shaft with respect to the base unit without swiveling the display body on the swiveling shaft in accordance with a posture of the base unit.

Furthermore, in the X-ray tube holding apparatus according to the present invention, the proximal end side of the X-ray tube is axially supported so as to enable its swiveling motion with respect to the swiveling shaft that extends from the based unit side toward the distal end side along a horizontal direction between the base unit and the display body and, on the other hand, the distal end side of the X-ray tube on the display body side is arranged on the same axial line as the swiveling shaft, and the X-ray tube that is arranged on the base unit side of the display body and swivels on the swiveling shaft is axially supported on a spindle that supports so as to enable a swiveling motion on the distal end side.

Moreover, in the X-ray tube holding apparatus according to the present invention, the X-ray tube is supported on a proximal-end-side fixing plate and a distal-end-side fixing plate between the base unit and the display body so as to be sandwiched between both the plates, the proximal-end-side fixing plate having a proximal end side thereof supported around the axis of the swiveling shaft and swiveling with a swiveling motion of the swiveling shaft, the distal-end-side fixing plate having a distal end side thereof arranged around an axis of the spindle arranged on the base unit side of the display body and swiveling with a swiveling motion of the swiveling shaft.

Additionally, in the X-ray tube holding apparatus according to the present invention, a plurality of frame materials supported by the proximal-end-side fixing plate and the distal-end-side fixing plate are arranged between both the fixing plates, and the X-ray tube arranged between the base unit and the display body is supported on the plurality of frame materials.

Further, in the X-ray tube holding apparatus according to the present invention, a coupling arm that is extended to the display body side from the base unit toward the display body so as to bypass the X-ray tube arranged on the axial line of the swiveling shaft between the base unit and the display body is used as the coupling body that enables coupling the base unit with the display body, a proximal end side of the coupling arm is supported on the base unit, and the display body is supported on a distal end side of the same in a fixed state.

Furthermore, in the X-ray tube holding apparatus according to the present invention, a coupling shaft that is arranged in parallel with the axial line of the swiveling shaft and the axial line of the spindle and penetrates the proximal-end-side fixing plate and the distal-end-side fixing plate to be axially supported by both the plates is used as the coupling body, a pinion that meshes with a proximal-end-side gear fixed to the base unit and is configured to rotate on its axis in a state that the coupling shaft rotates around the proximal-end-side gear with swiveling of the proximal-end-side fixing plate and the distal-end-side fixing plate with respect to the axial line of the swiveling shaft and the axial line of the spindle is axially supported on the base unit side of the coupling shaft, and a pinion that meshes with a distal-end-side gear fixed on the base unit side of the display body and is configured to rotate on its axis in a state that the coupling shaft rotates around the distal-end-side gear with swiveling of the proximal-end-side fixing plate and the distal-end-side fixing plate with respect to the axial line of the swiveling shaft and the axial line of the spindle is axially supported on the distal end side of the coupling shaft.

Moreover, in the X-ray tube holding apparatus according to the present invention, the proximal-end-side gear and the distal-end-side gear have the same outer diameter and the same tooth shape/number of teeth, central axes of the gears are set on the same axial line as the axial line of the swiveling shaft and the axial line of the spindle, and the pinions that mesh with these gears are formed with the same outer diameter and the same tooth shape/number of teeth.

Additionally, in the X-ray tube holding apparatus according to the present invention, the display body includes an operation unit that enables an operator who is on the distal end side of the X-ray tube with respect to the base unit to swivel the X-ray tube with respect to at least the base unit, translate the same with respect to the ceiling or the floor surface, move up and down the same with respect to the ceiling or the floor surface, or swivel the same on the axial line of the vertical shaft.

Effect of the Invention

According to the present invention, even if the X-ray tube is swiveled to change a posture, the operator can be prevented from erroneously recognizing imaging relevant information or erroneously operating the X-ray tube holding apparatus, thereby improving operability of the X-ray tube holding apparatus and enabling rapid and accurate photography.

BRIEF DESCRIPTION OF DRAWINGS

FIG. 7(a) is a front view showing arrangement of the X-ray tube, the operation handle, and the display body in an initial state and FIG. 7(b) is front view showing a state that the X-ray tube and the operation handle are swiveled 90 degrees with respect to the base unit;

FIG. 10(a) is a front view showing arrangement of a display body and an imaging unit in an initial state in the conventional X-ray tube holding apparatus and FIG. 10(b) is a front view showing arrangement when the display body and the imaging unit are swiveled 90 degrees with respect to the initial state in the conventional X-ray tube holding apparatus;

EXPLANATIONS OF LETTERS OR NUMERALS

Figure 1:
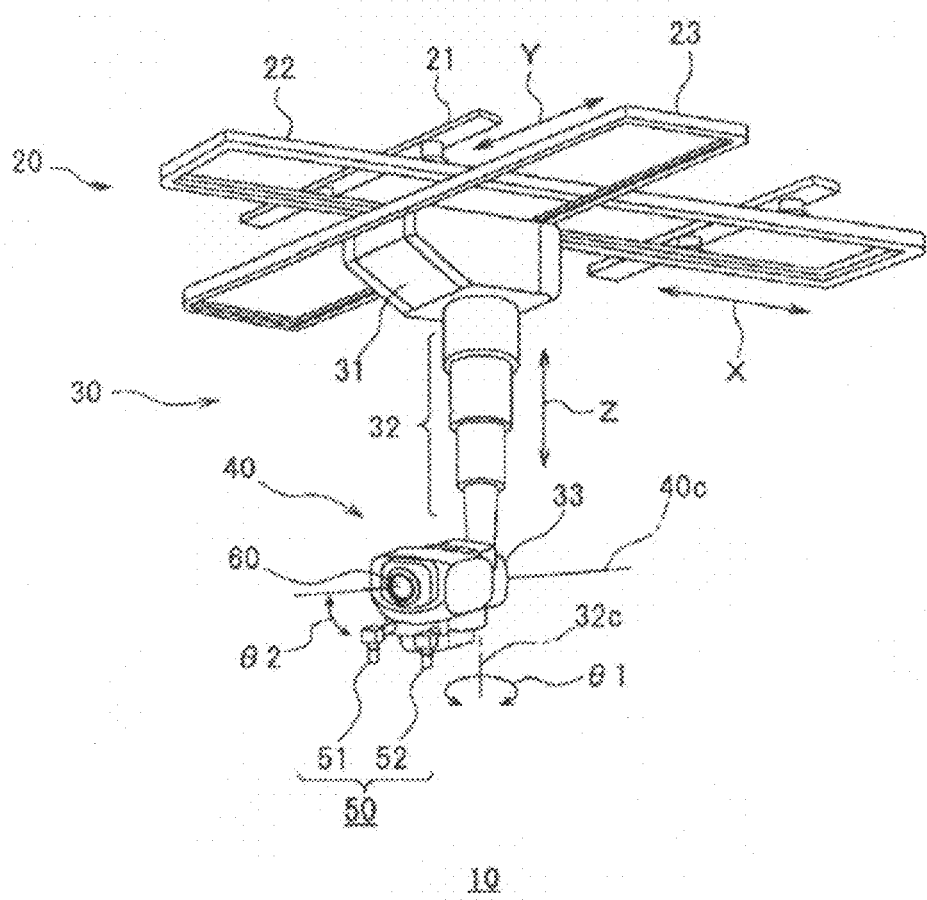
FIG. 1 is a perspective view showing a configuration of an X-ray tube holding apparatus according to an embodiment of the present invention.

10 X-ray tube holding apparatus
20 mount
21 support
22 X rail
23 Y rail
30 elevating shaft
31 connecting base unit
32 shaft unit
32c axial line
33 base unit
36 shaft
37 base-unit-side gear
40 X-ray tube
40c swiveling axis
41 X-ray tube housing
42 imaging unit
44 coupling shaft
45, 46 pinion
48 bearing
50 operation handle
51, 52 handle unit
53, 54 operation unit
60 display body
61 display panel
66 shaft
67 display-body-side gear
M step motor

BEST MODE(S) FOR CARRYING OUT THE INVENTION

An X-ray tube holding apparatus according to an embodiment of the present invention will now be described hereinafter in detail with reference to the drawings. Although the X-ray tube holding apparatus according to the following embodiment corresponds to a case that the present invention is applied to an X-ray tube holding apparatus which is of a type that is hung from a ceiling, the present invention is not restricted thereto, and it can be applied to a type that travels on a floor surface by using a carriage to move in an XY direction or a type that can be translated on a rail fixed on the floor surface.

As shown in FIG. 1, the X-ray tube holding apparatus according to this embodiment includes a mount 20, an elevating shaft 30, a base unit 33, an X-ray tube 40, an operation handle 50, and a display body 60. Here, FIG. 1 is a perspective view showing a configuration of the X-ray tube holding apparatus 10 according to this embodiment. The detailed configuration of each member will now be described hereinafter.

The mount 20 includes an X rail 22 that is fixed to a support 21 fixed on a ceiling (not shown) and arranged to extend in an X direction within a plane horizontal to a ceiling surface and a Y rail 23 that is fixed to be movable in the X direction with respect to this X rail 22 and arranged to extend in a Y direction within the plane horizontal to the ceiling surface. That is, the mount 20 can be translated in the X direction and the Y direction with respect to the ceiling.

A connecting base unit 31 is disposed to the Y rail 23, and an elevating shaft 30 as a vertical shaft is attached to the connecting base unit 31. The connecting base unit 31 can move in the Y direction with respect to the Y rail 23. Since the Y rail 23 can relatively move with respect to the X rail 22, the connecting base unit 31 can horizontally move with respect to the ceiling.

The elevating shaft 30 includes the connecting base unit 31, a shaft unit 32, and a base unit 33. The shaft unit 32 vertically extends downwards from the connecting base unit 31 so that a lower end side of the connecting base unit 31 can be extended/contracted in the vertical direction at a proximal end thereof. Here, as a mechanism that extends/contracts the shaft unit 32, a known configuration is utilized, thereby omitting a description thereof.

The base unit 33 is fixed at the lower end of the shaft unit 32 so that it can swivel (an angle $\theta 1$) on an axial line 32c of the shaft unit 32, and the base unit 33 can move up and down (a Z direction) based on extraction/contraction of the shaft unit 32, can be translated with respect to the ceiling along the X rail 22 and the Y rail 23, and can swivel in the $\theta 1$ direction.

Figure 2:
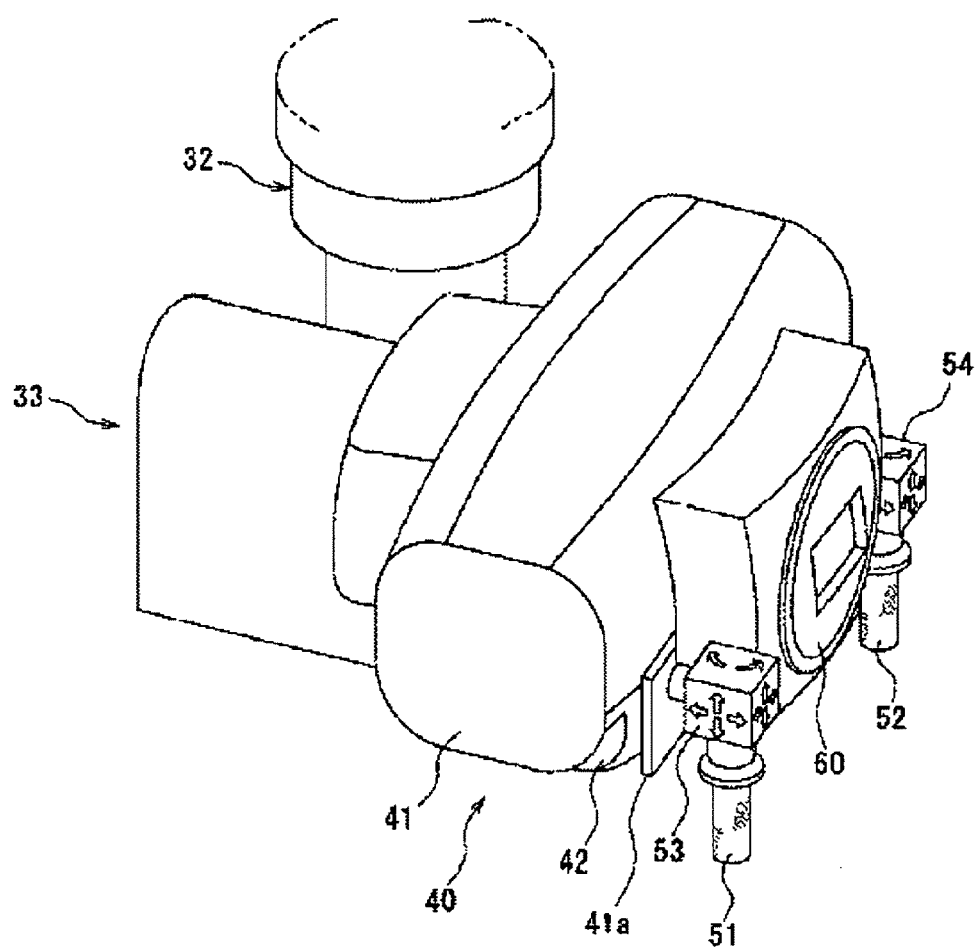
FIG. 2 is a perspective view showing arrangement of a shaft unit, a base unit, an X-ray tube, an operation handle, and a display body according to the embodiment of the present invention from a front side surface.
Figure 3:
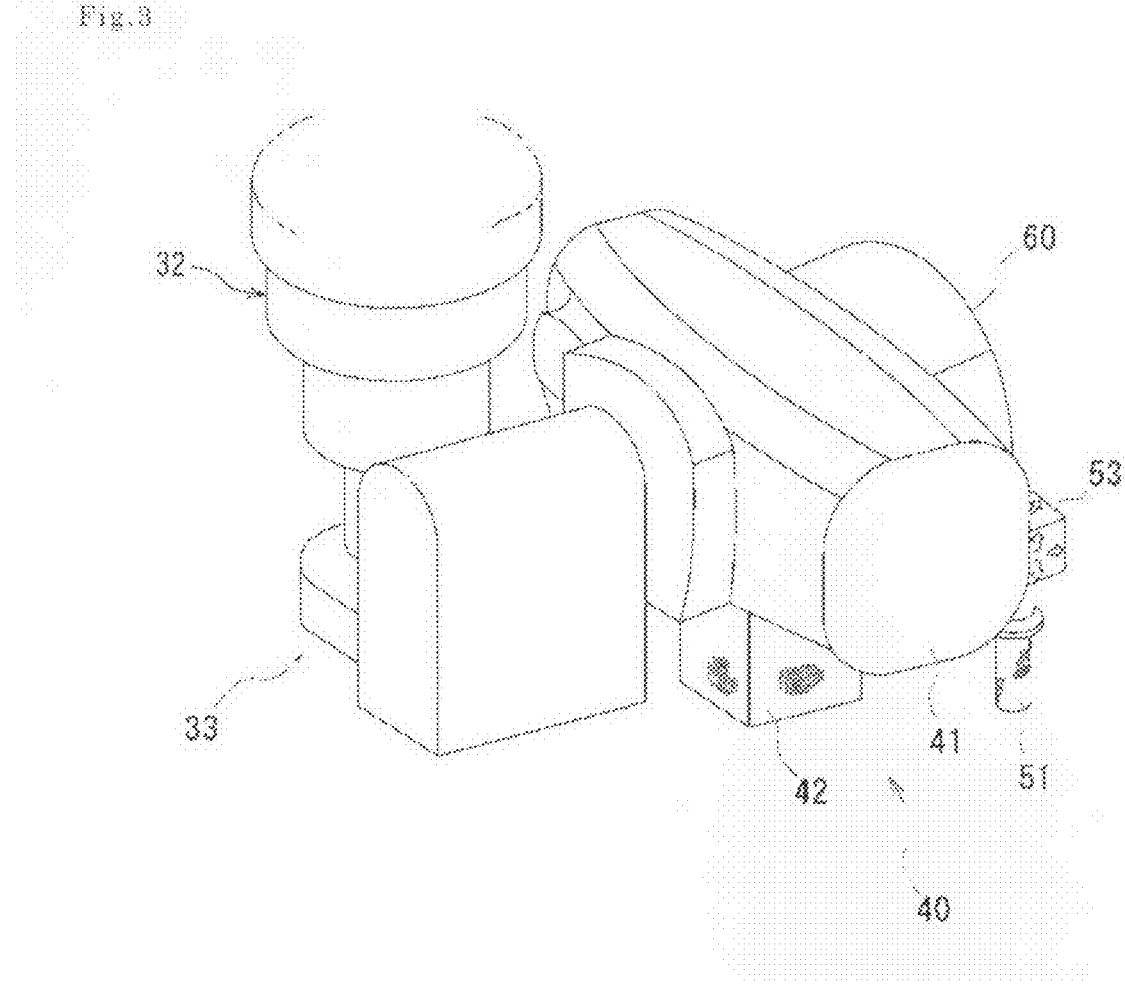
FIG. 3 is a perspective view showing the shaft unit, the base unit, the X-ray tube, the operation handle, and the display body according to the embodiment of the present invention from a rear side surface.

As shown in FIGS. 2 and 3, an X-ray tube 40 is disposed to the base unit 33 on a distal end side in a radiating direction with the base unit 33 at the center in the horizontal direction. That is, the X-ray tube 40 is vertical to the axial line 32c of the shaft unit 32 with respect to the base unit 33, extends to the distal end side in the horizontal direction from the base unit 33 side, and can swivel (an angle $\theta 2$) around a swiveling shaft 40c that runs through a predetermined position of the X-ray tube 40. The X-ray tube 40 includes an X-ray tube housing 41 and an imaging unit 42. The imaging unit 42 is fixed in the X-ray tube housing 41 (FIG. 6) and can apply an X-ray toward a photography subject in a lower portion in FIG. 7(a) to obtain a desired image. Here, FIG. 2 is a perspective view showing arrangement of the shaft unit 32, the base unit 33, the X-ray tube 40, the operation handle 50, and the display body 60 from a front side surface. FIG. 3 is a perspective view showing arrangement of the shaft unit 32, the base unit 33, the X-ray tube 40, the operation handle 50, and the display body 60 from a rear side surface. FIGS. 2 and 3 show an initial state that the X-ray tube 40 and the operation handle 50 are not swiveled with respect to the base unit 33.

Figure 5:
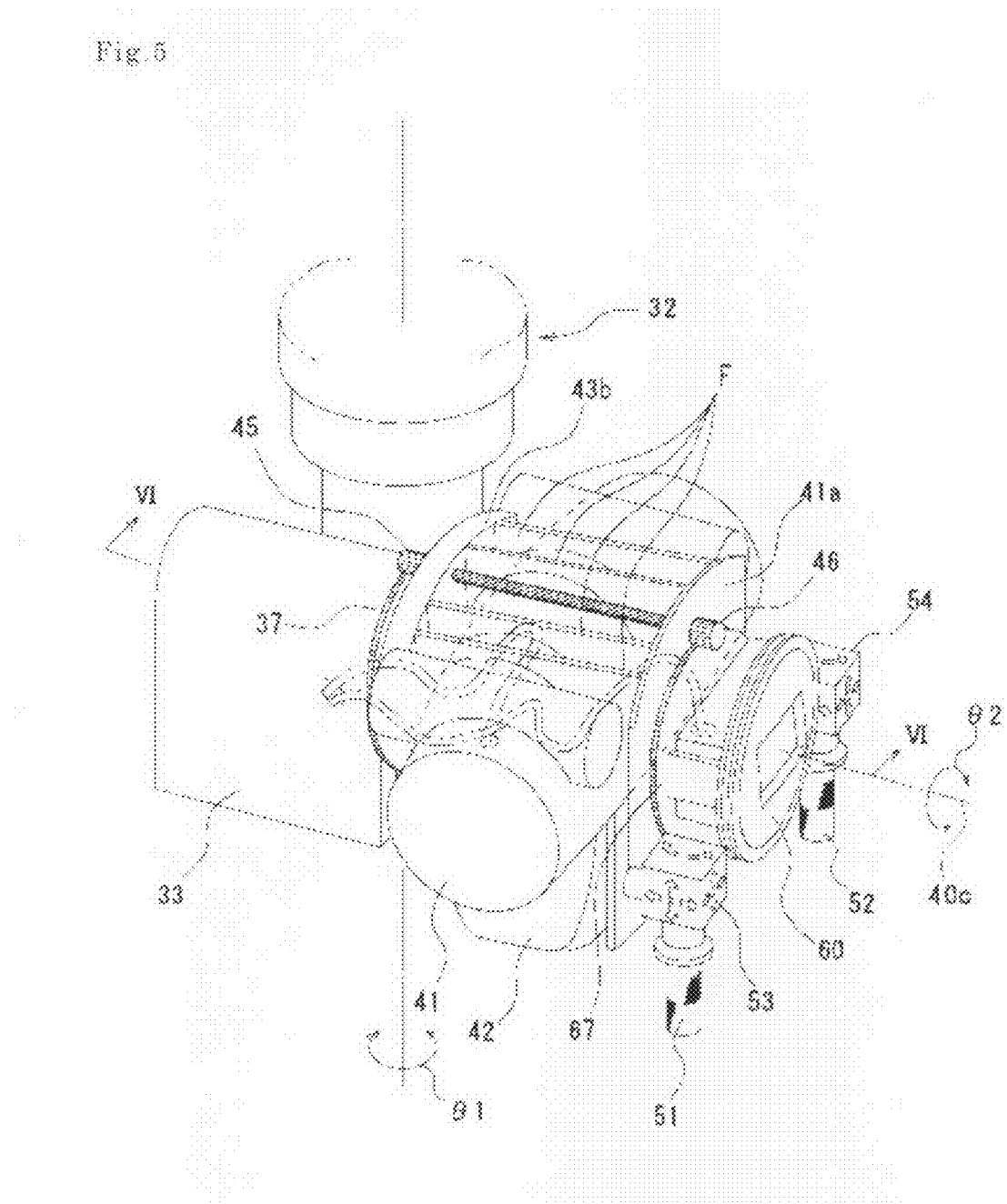
FIG. 5 is a perspective view showing an internal configuration of the X-ray tube according to the embodiment of the present invention from the front side surface.
Figure 6:
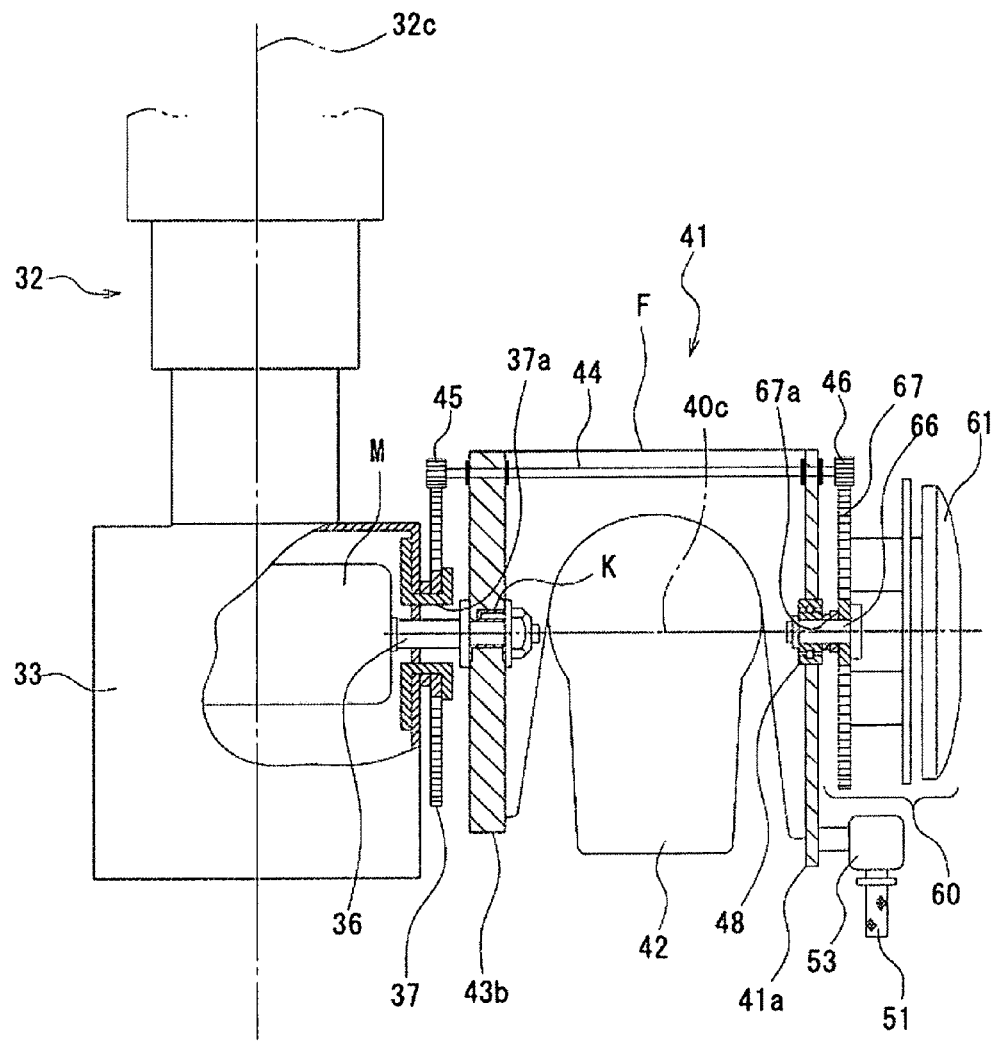
FIG. 6 is a cross-sectional view taken along a line VI-VI in FIG. 5.
Figure 8:
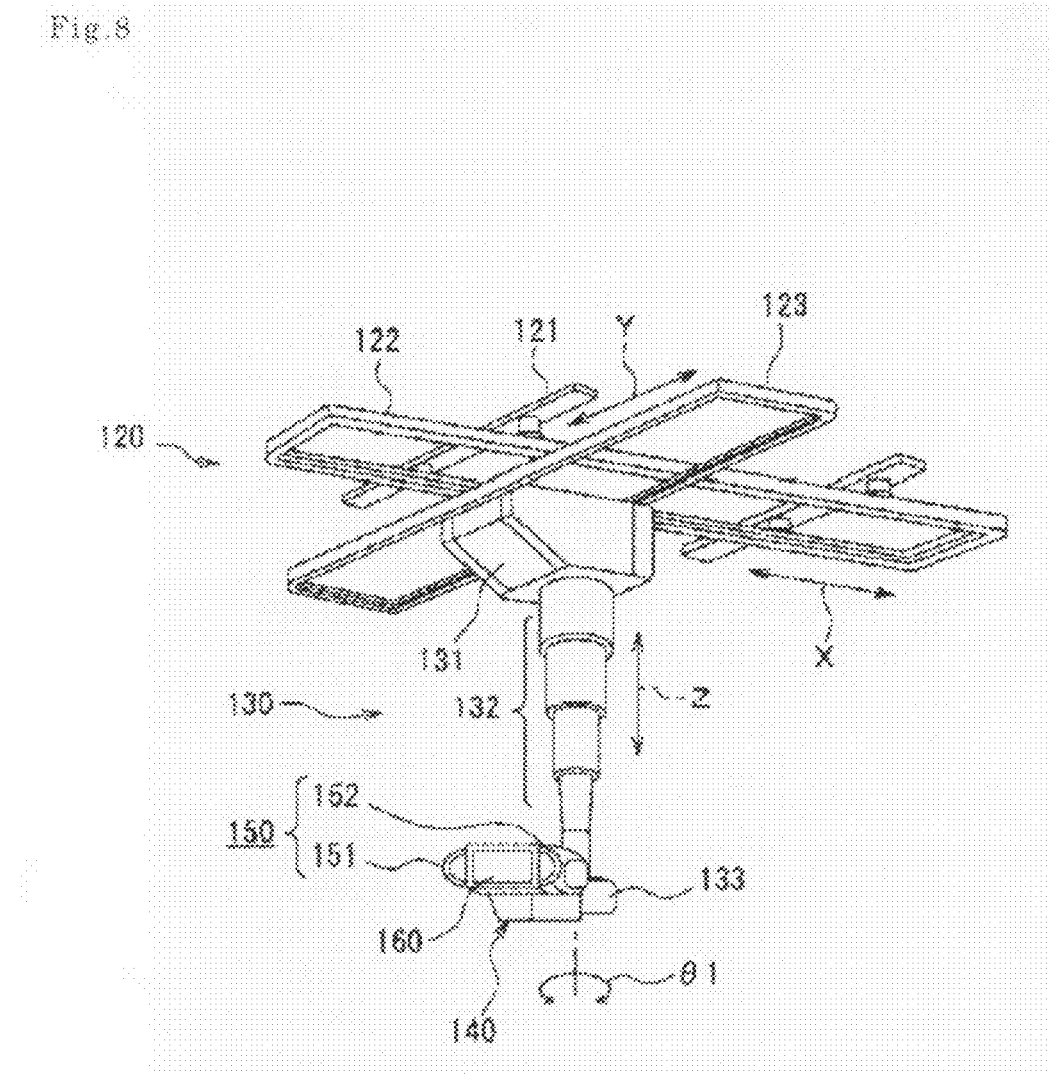
FIG. 8 is a perspective view showing a configuration of a conventional ceiling hung type X-ray tube holding apparatus.
Figure 9:
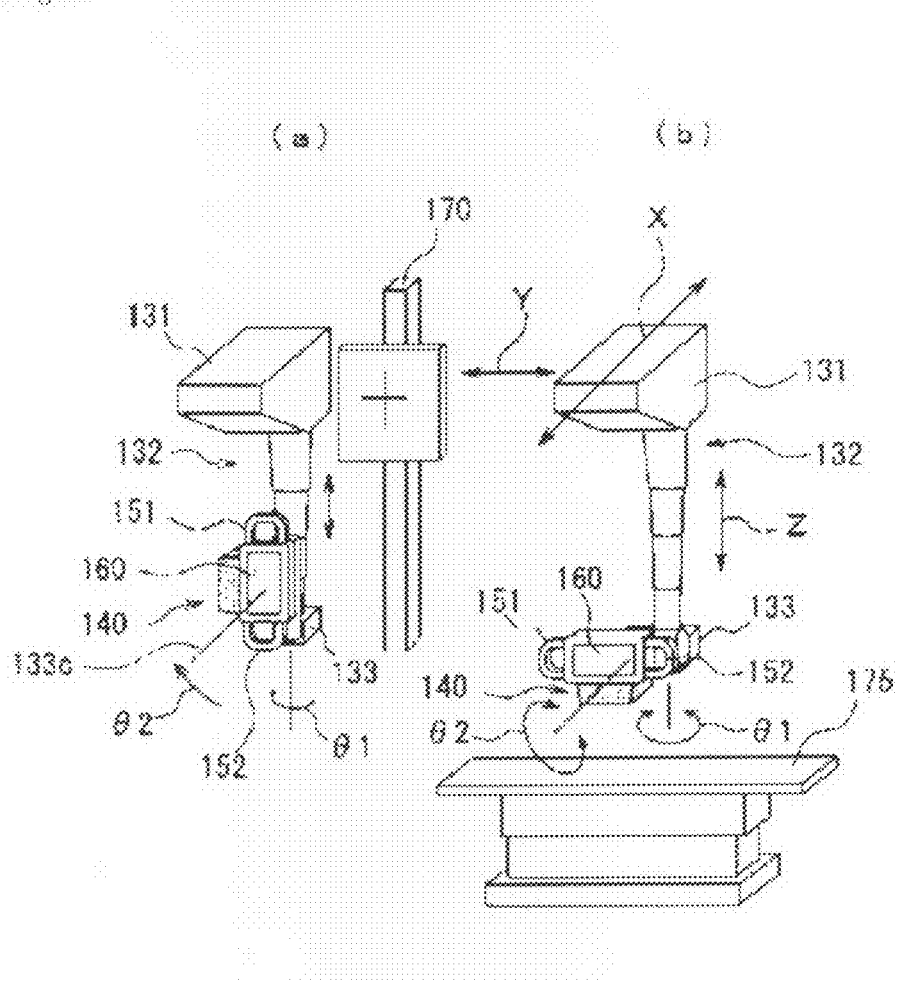
FIG. 9(a) is a perspective view showing a state that the conventional X-ray tube holding apparatus and an upright photography platform are utilized to perform photography and FIG. 9(b) is a perspective view showing a state that the conventional X-ray tube holding apparatus and a horizontal photography platform are utilized to effect photography.
Figure 11:
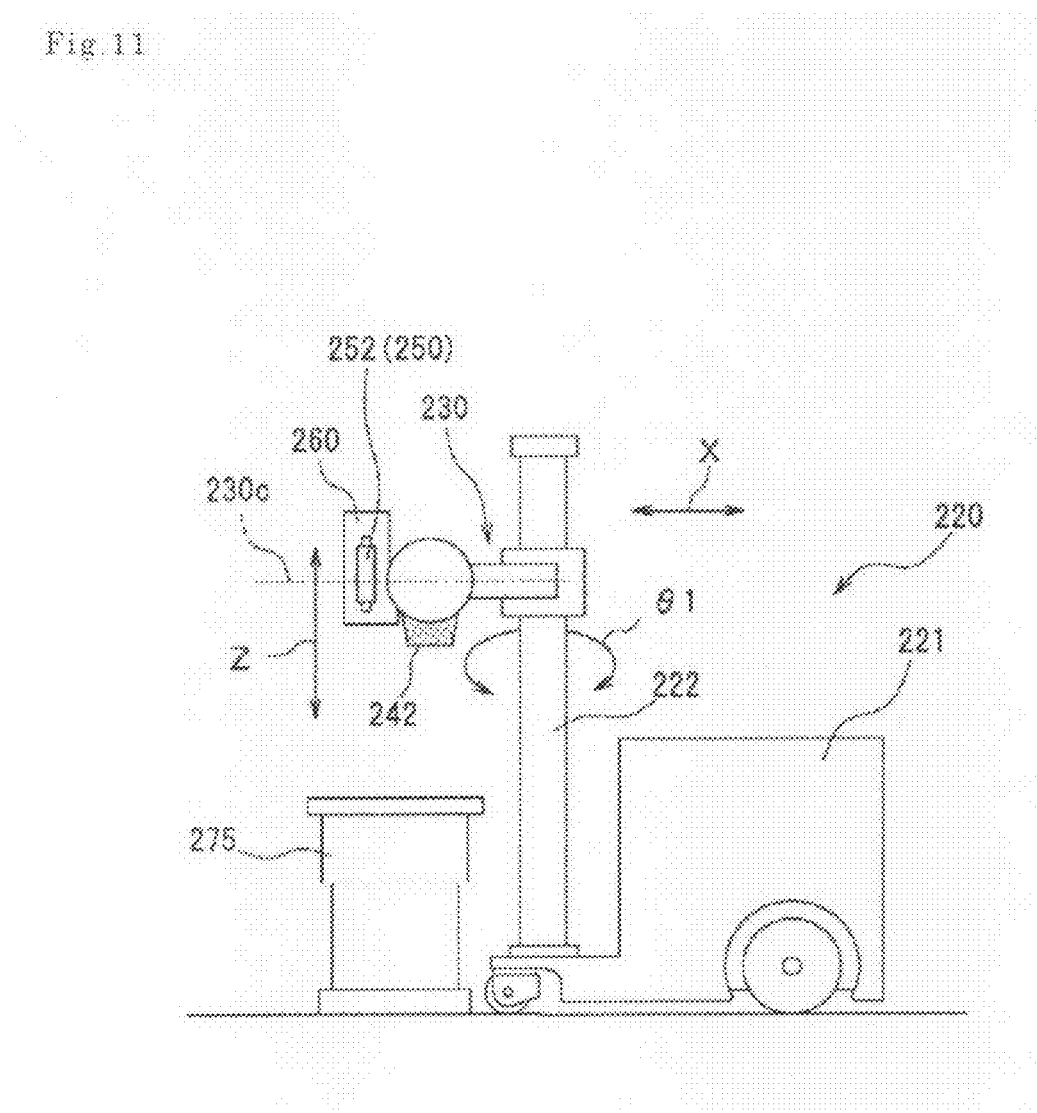
FIG. 11 is a side view showing a configuration of a conventional floor traveling type X-ray photography apparatus.
Figure 12:
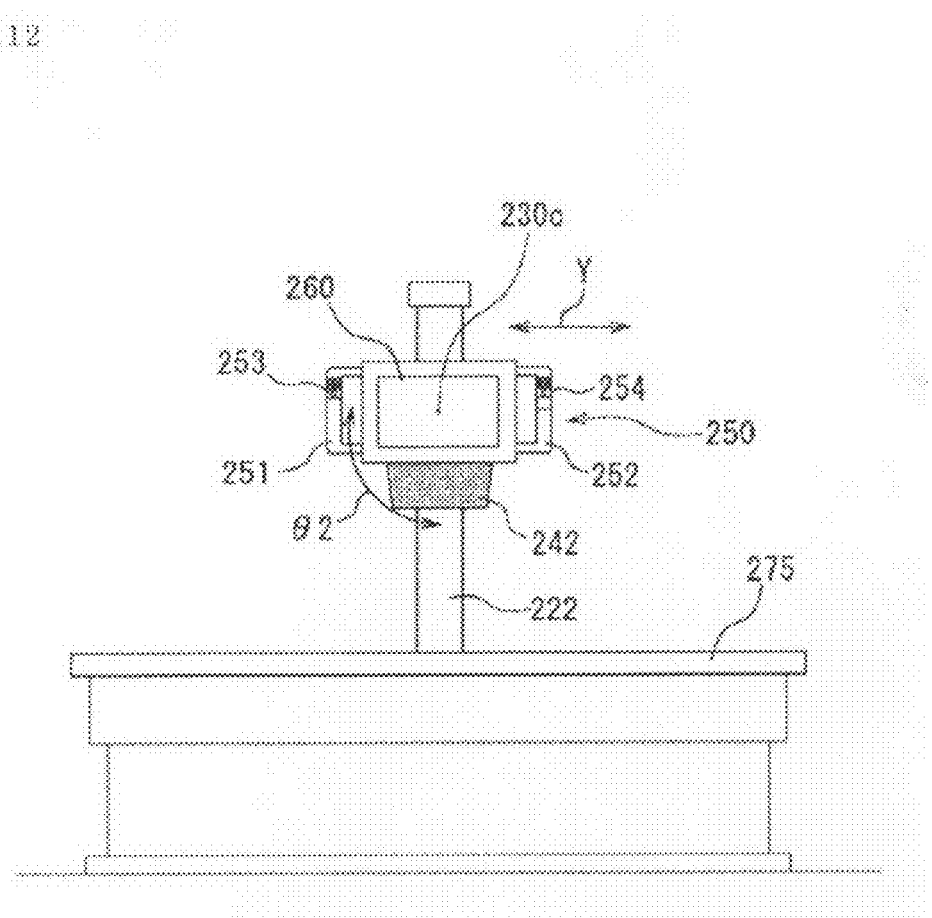
FIG. 12 is a front view showing a configuration of the conventional floor traveling type X-ray photography apparatus.

In the X-ray tube 40 and the X-ray tube housing 41 covering this tube, a proximal-end-side fixing plate 43b is arranged on a base unit proximal end side between the members 40 and 41 and the base unit 33 and a distal-end-side fixing plate 41a is arranged on a back surface side of the display body 60 between the base unit 33 and the display body 60 in an upright state that these plates are orthogonal to the axial line of the swiveling shaft 40c of the X-ray tube 40 as shown FIGS. 5 and 6. As depicted in FIG. 6, in the base unit 33, a step motor M is arranged, and a swiveling shaft 36 of the motor M is extended/arranged toward the distal end side from a hole portion 37a along the swiveling shaft 40C of the X-ray tube 40. The proximal-end-side fixing plate 43b is axially supported on the swiveling shaft 36 of the step motor M through a key K in a fixed state. That is, the proximal-end-side fixing plate 43b can swivel around an axis of the swiveling shaft 40c of the X-ray tube 40 with swiveling around the axis of the swiveling shaft 36 based on driving by the step motor M.

On the other hand, the distal-end-side fixing plate 41a provided on the display body 60 side of the X-ray tube 40 is arranged at the center of the base unit 33 side (a back surface side) of the display plate 60 as shown in FIG. 6 and axially supported with respect to a spindle 66 fixed and arranged on the same axial line as the swiveling shaft 40c of the X-ray tube 40 via a bearing 48.

That is, the X-ray tube 40 (also including the X-ray tube housing 41) arranged between the base unit 33 and the display body 60 is supported by both the fixing plates 43b and 41a to be sandwiched between these two fixing plates 43b and 41a and, giving more specific explanation, the X-ray tube 40 is supported by the respective fixing plates 43b and 41a in a state that both ends thereof are held by a plurality of frame materials F supported by the respective fixing plates 43b and 41a (see FIGS. 5 and 6).

As a result, all of the X-ray tube 40, the X-ray tube housing 41, and the respective fixing plates 43b and 41a can swivel on the swiveling shaft 40c of the X-ray tube 40 in the θ2 direction based on, e.g., driving of the step motor M in association with swiveling driving of the swiveling shaft 36.

Respective end portions, i.e., a distal end and a proximal end of the X-ray tube 40 supported between the proximal end side for the base unit 33 and the back surface side of the display body 60 on the distal end side for the base unit 33 so as to allow its swiveling motion between the respective shafts 36 and 66 are actually supported by the respective shafts 36 and 66 without penetration of the swiveling shaft 40c of the X-ray tube 40 that is present as an entity in an X-ray tube lamp arranged inside, and the X-ray tube 40 is swiveled around the virtually set swiveling shaft 40c in the θ2 direction.

Figure 4:
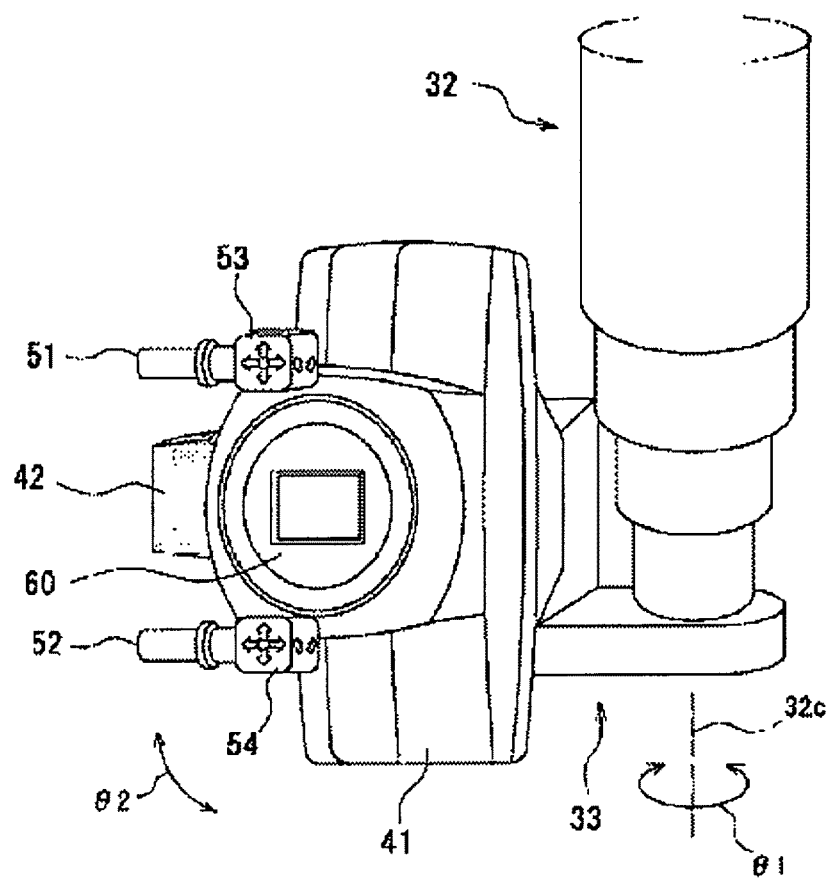
FIG. 4 is a front view showing a state that the X-ray tube and the operation handle according to the embodiment of the present invention are swiveled 90 degrees with respect to the base unit.

The operation handle 50 is disposed to the display body 60 side of the distal-end-side fixing plate 41a. The operation handle 50 includes operation units 53 and 54 fixed on both left and right ends of the distal-end-side fixing plate 41a of the X-ray tube housing 41 and handle units 51 and 52 extending downwards from the operation units 53 and 54, respectively, so as to sandwich the display body 60. Each of the operation units 53 and 54 includes switches associated with translation, vertical movement and swiveling on a side surface thereof. When an operator of the X-ray tube holding apparatus 10 operates this surface of each of the operation units 53 and 54 in response to a desired operation, the X-ray tube 40, the operation handle 50 and the display body 60 perform translation, vertical movement and/or swiveling. For example, as shown in FIG. 4, when the X-ray tube 40 and the operation handle 50 are rotated 90 degrees (θ2=90) around the swiveling shaft 40c of the X-ray tube 40, an irradiating direction of the imaging unit 42 can be set to the horizontal direction. FIG. 4 is a front view showing a state that the X-ray tube 40 and the operation handle 50 are swiveled 90 degrees with respect to the base unit 33.

The display body 60 includes a display panel 61 on a front surface thereof. The display panel 61 displays imaging relevant information (e.g., information concerning photography conditions or a photography subject). As this display panel 61, a liquid crystal touch panel can be used. Here, an operator (e.g., an X-ray operator) is on the distal end side of the display panel 61 of the display body 60. That is, the operator stands on a floor surface in a photography room while facing the display body 60 along a direction of the base unit 33 on the distal end side of the X-ray tube 40 apart from the base unit 33, and he/she operates the operation units 53 and 54 of the operation handle 50 while visually confirming imaging relevant information displayed in the display panel 61. Additionally, the operator can operate a touch sensor displayed in the display panel 61 of the display body 60 and can also operate switches S (the operation unit: FIG. 7) that are arranged in a peripheral portion of the display panel 61 and associated with translation, vertical movement and swiveling of the X-ray tube 40 like the switches arranged in the operation units 53 and 54 as shown in FIGS. 7(a) and (b).

Here, referring to FIG. 5 and FIG. 6 in the drawings, a description will be given as to a mechanism that maintains a posture of the display body 60 without swiveling the display body 60 on the swiveling shaft 36 in accordance with a posture of the base unit 33 even in a state that the mechanism is arranged between the base unit 33 and the display body 60 to couple the display body 60 with the base unit 33 and the X-ray tube 40 is swiveled on the swiveling shaft 40c with respect to the base unit 33 with the mechanism being axially supported on the swiveling shaft 36 between the base unit 33 and the display body 60 to bypass the swiveling shaft 40C of the X-ray tube 40 that is virtually set between the base unit 33 and the display body 36. That is, this mechanism can couple the base unit 33 and the display body 60 with each other, enables the X-ray tube 40 and the operation handle 50 engaged with this tube to swivel on the swiveling shaft 40c of the X-ray tube 40 in the θ2 direction while maintaining the posture of the display body 60 like the base unit 33, and couples the base unit 33 and the display body 60 with each other so as to maintain a posture of the display body 60 in accordance with a posture of the base unit 33.

A base-unit-side gear 37 is fixed on an outer surface of the base unit 33 on the X-ray tube housing 41 side in a state that it is supported by the base unit 33. On the other hand, a display-body-side gear 67 is fixed on a back surface of the display body 60 on the X-ray tube housing 41 side in a state that it is supported by the display body 60. Here, the base-unit-side gear 37 and the display-body-side gear 67 are formed on outer peripheries of circular plates having the same outer diameter, tooth shapes and numbers of teeth at the same pitch, and hole portions 37a and 67a piercing in a thickness direction are formed at the centers, respectively. One end of the spindle 66 associated with the swiveling shaft 40c is inserted and fixed in the hole portion 67a, and the spindle 66 can support the distal-end-side fixing plate 41a on the proximal end side so as to enable its swiveling motion with the bearing 48 interposed therebetween. On the other hand, the shaft 36 extending from the step motor M fixed on the base unit 33 is inserted in the hole portion 37a on the base unit 33 side in such a manner that the axial line is provided on the swiveling shaft 40c. The proximal-end-side fixing plate 43b is axially supported on the distal end side of this shaft 36 in a fixed state through the key K, thereby supporting the proximal-end-side fixing plate 43b so as to enable its swiveling motion with respect to the base unit 33.

In particular, a lamp of the X-ray tube 40 is present in the X-ray tube housing 41 between the base unit 33 and the display body 60, and a coupling shaft 44 that reaches outer peripheral positions of the display-body-side gear 67 and the base-unit-side gear 37 are inserted and fixed at an upper position between the proximal-end-side fixing plate 43b and the distal-end-side fixing plate 41a that does not interfere with the X-ray tube 40 or the imaging unit 42 so as to upwardly bypass the placed swiveling shaft 40c. That is, the coupling shaft 44 as a coupling body is arranged between the display body 60 and the base unit 33 and couples both the members with each other. Further, the coupling shaft 44 holds the X-ray tube 40 and the X-ray tube housing 41 between the proximal-end-side fixing plate 43b and the distal-end-side fixing plate 41a. Pinions 45 and 46 are axially supported on respective end portions of the coupling shaft 44 that penetrates the proximal-end-side fixing plate 43b and the distal-end-side fixing plate 41a to be supported by both the plates 43b and 41a so as to upwardly bypass the swiveling shaft 40c of the X-ray tube 40 in this manner, and the base-unit-side gear 37 and the display-body-side gear 67 mesh with the coupling shaft 44 in an associated manner, respectively. Here, the respective pinions 45 and 46 are formed with tooth shapes and number of teeth at the same pitch.

Here, the mechanism that maintains the posture of the display body 60 without swiveling the display body 60 on the swiveling shaft 36 in accordance with the posture of the base unit 33 even in a state that the X-ray tube 40 is swiveled on the swiveling shaft 40c with respect to the base unit 33 is formed of the base-unit-side gear 37, the coupling shaft 44, the pinions 45 and 46, and the display-body-side gear 67. That is, even in a state that the X-ray tube 40 and the operation handle 50 swivel on the swiveling shaft 40c in the X-ray tube 40 in the θ2 direction, the display body 60 on the front side of the operator does not swivel in the θ2 direction and maintains the same posture as the base unit 33. As a result, the X-ray tube 40 and the operation handle 50 that are present between the base unit 33 and the display body 60 having the operator standing on the front side thereof and have such a positional relationship can swivel on the swiveling shaft 40c in the θ2 direction by an operation of the operation handle 50 while maintaining the posture of the display body 60.

Giving a detailed description on this mechanism, the coupling shaft 44 is supported by the base unit 33 through the pinion 45 and the base-unit-side gear 37, and it supports the display body 60 through the pinion 46 and the display-body-side gear 67. Further, the coupling shaft 44 is arranged in such a manner that axial lines of the shaft 36 and the shaft 66 are arranged on the swiveling shaft 40c and the axial lines become parallel to the swiveling shaft 40c. Therefore, when the operation handle 50 is operated, the step motor M is driven, whereby the shaft 36 is driven to rotate and the X-ray tube 40 and the operation handle 50 swivel on the swiveling shaft 40c in the θ2 direction. Based on this movement, the pinions 45 and 46 rotate and move while meshing with the outer peripheries of the base-unit-side gear 37 and the display-body-side gear 67, respectively. Furthermore, since the X-ray tube housing 41 and the display body 60 are coupled with each other through the bearing 48, the display-body-side gear 67 rotates on its axis around the display-body-side gear 67 for a distance corresponding to a trajectory of movement of the pinion 46. Likewise, since the base-unit-side gear 37 can relatively swivel with respect to the base unit 33, it rotates on its axis around the shaft 36 for a distance corresponding to a trajectory of rotational movement of the pinion 45. That is, the pinion 45 that meshes with the proximal-end-side gear 37 fixed on the base unit 33 side of the coupling shaft 44 can rotate on its axis in a state that the coupling shaft 44 rotates around the proximal-end-side gear 37 as the proximal-end-side fixing plate 43b and the distal-end-side fixing plate 41a swivel on the axial line 40c. On the other hand, the pinion 46 that meshes with the distal-end-side gear 67 fixed on the distal end side of the coupling shaft 44 can rotate on its axis in a state that the coupling shaft 44 rotates around the distal-end-side gear 67 as the proximal-end-side fixing plate 43b and the distal-end-side fixing plate 41a swivel on the axial line 40c in the θ2 direction.

Therefore, when the X-ray tube 40 and the operation handle 50 are swiveled on the swiveling shaft 40c to direct the imaging unit 42 to a desired direction by manipulating the operation units 53 and 54 of the operation handle 50 or the switches S (the operation unit: FIG. 7) arranged in the peripheral portion of the display panel 61 in the display body 60, the posture of the display body 60 can be maintained constant in accordance with the posture of the base unit 33 irrespective of this swiveling. That is, even in a state that the operator swivels the X-ray tube 40 placed on the distal end side in the radiating direction with respect to the base unit 33 toward the θ2 direction, the posture of the display body 60 provided on the distal end side distanced from the X-ray tube 40 is not changed, the operator who stands on the front surface side of the display body 60 can operate the operation units 53 and 54 of the operation handle 50 or the switches S while visually confirming imaging relevant information displayed in the display panel 61 of the display body 60, and the posture of the display body 60 can be maintained constant with respect to the posture of the base unit 33 at this moment. For example, a posture of the display body 60 in such a state that it is swiveled 90 degrees as shown in FIG. 7(b) is not changed with respect to the initial state depicted in FIG. 7(a). Therefore, since the posture of the display body 60 is constant even though a direction of the X-ray tube 40 is changed, the operator who stands on the front surface side of the display body 60 and visually confirms imaging relevant information displayed in the display panel 61 does not erroneously recognize display contents in the display body 60 or perform an erroneous operation. Here, FIG. 7(a) is a front view showing arrangement of the X-ray tube 40, the operation handle 50, and the display body 60 in the initial state, and (b) is a front view showing a state that the X-ray tube 40 and the operation handle 50 are swiveled 90 degrees with respect to the base unit 33.

In the X-ray tube holding apparatus 10 according to this embodiment, although a combination of gears, i.e., the base-unit-side gear 37, the pinion 45, the display-body-side gear 67, and the pinion 46 is used, a combination of a chain and a sprocket or a combination of a belt and a pulley can be adopted instead. Moreover, although the gears 37 and 67 and the gears 45 and 46 are formed with tooth shapes and the numbers of teeth at the same pitch in the foregoing embodiment, both the mechanical elements do not have to be based on the same conformation, and they are not restricted to such configurations as long as the display body is a mechanism that can be fixed in synchronization with the base unit side.

Since the above-described configuration is adopted, according to the foregoing embodiment, even in a state that the operator grasps the operation handle 50 to move the X-ray tube 40 in the X direction, the Y direction, and the Z direction in the imaging room and the X-ray tube 40 is swiveled (oscillated) in the θ2 direction to direct the imaging unit 42 of the X-ray tube 40 to the upper side for the photography subject, the display body 60 that is visually recognized by the operator is not swiveled, and imaging relevant information displayed in the display body 60 can be appropriately grasped, thereby improving operability of the X-ray tube holding apparatus 10.

Although the present invention has been described with reference to the foregoing embodiment, the present invention is not restricted to the foregoing embodiment, and it can be improved or changed for the purpose of improvement or within the scope of the concept of the present invention. For example, although all of the X-ray tube 40, the X-ray tube housing 41, and the respective fixing plates 43b and 41a are axially supported on the swiveling shaft 36 of the step motor M on the proximal end side of the base unit 33 and the distal end side is axially supported on the spindle 66 in the foregoing embodiment, the X-ray tube 40 may be axially supported on the swiveling shaft 36 alone in a cantilever manner and a coupling body that can couple the base unit 33 and the display body 60 with each other may be arranged without using, e.g., a coupling shaft as a coupling body like the embodiment. In this case, the coupling body may be a cantilever coupling arm that is extended on the display body 60 side from the base unit 33 to the display body 60 so as to bypass the X-ray tube 40 arranged on the axial line of the swiveling shaft 40c between he base unit 33 and the display body 60, and it may be configured to support the proximal end side on the base unit 33 and support the display body 60 on the distal end side in a fixed state.

The invention claimed is:

1. An X-ray tube holding apparatus comprising:
   a mount configured to be translated with respect to a ceiling or a floor surface;
   a vertical shaft arranged in a vertical direction with respect to the mount;
   a base unit configured to swivel on an axial line of the vertical shaft and move up and down;
   an X-ray tube that is provided on a distal end in an irradiating direction with the base unit, the base unit being axially supported to allow swiveling motion on a swiveling shaft along a horizontal direction, and the base unit including an imaging unit for supplying an X-ray from the X-ray tube toward a photography subject;
   a display body disposed distanced from the X-ray tube with respect to the base unit, provided on a distal end of the X-ray tube, enables visual recognition when facing an operator who is directed to the base unit, and displays imaging relevant information, the X-ray tube being configured to be swiveled with respect to at least the base unit, translated with respect to the ceiling or the floor surface, moved up and down with respect to the ceiling or the floor surface, or swiveled on the axial line of the vertical shaft by the operator at the distal end of the X-ray tube, wherein an X-ray tube holding apparatus including a coupling body that is axially supported on the swiveling shaft between the base unit and the display body, arranged between the base unit and the display body so as to bypass the X-ray tube arranged on the axial line of the swiveling shaft between the base unit and the display body, and enables coupling the base unit with the display body so as to maintain a posture of the display body even in a state that the display body is coupled with the base unit and the X-ray tube is swiveled on the swiveling shaft with respect to the base unit without swiveling the display body on the swiveling shaft in accordance with a posture of the base unit; and
   a coupling arm of the coupling body extending to the display body from the base unit toward the display body for enabling coupling of the base unit with the display body, a proximal end of the coupling arm being supported on the base unit, and the display body being supported on a distal end of the coupling arm in a fixed state.

2. The X-ray tube holding apparatus according to claim 1, wherein the display body includes an operation unit that enables an operator who is on the distal end of the X-ray tube with respect to the base unit to swivel the X-ray tube with respect to at least the base unit, translate the X-ray tube with respect to the ceiling or the floor surface, move up and down the X-ray tube with respect to the ceiling or the floor surface, or swivel the X-ray tube on the axial line of the vertical shaft.

3. An X-ray tube holding apparatus comprising:
   a mount configured to be translated with respect to a ceiling or a floor surface;
   a vertical shaft arranged in a vertical direction with respect to the mount;
   a base unit configured to swivel on an axial line of the vertical shaft and move up and down;
   an X-ray tube provided on a distal end in an irradiating direction with the base unit, the base unit being axially supported to allow swiveling motion on a swiveling shaft along a horizontal direction, and including an imaging unit for supplying an X-ray from the X-ray tube toward a photography subject;
   a display body disposed to the distal end distanced from the X-ray tube with respect to the base unit, provided on the distal end of the X-ray tube, enables visual recognition when facing an operator who is directed to the base unit, and displays imaging relevant information, the X-ray tube being configured to be swiveled with respect to at least the base unit, translated with respect to the ceiling or the floor surface, moved up and down with respect to the ceiling or the floor surface, or swiveled on the axial line of the vertical shaft by the operator at the distal end of the X-ray tube, wherein an X-ray tube holding apparatus including a coupling body that is axially supported on the swiveling shaft between the base unit and the display body, arranged between the base unit and the display body so as to bypass the X-ray tube arranged on the axial line of the swiveling shaft between the base unit and the display body, and enables coupling the base unit with the display body so as to maintain a posture of the display body even in a state that the display body is coupled with the base unit and the X-ray tube is swiveled on the swiveling shaft with respect to the base unit without swiveling the display body on the swiveling shaft in accordance with a posture of the base unit,
   a proximal end of the X-ray tube being axially supported so as to enable swiveling motion with respect to the swiveling shaft, the distal end of the X-ray tube being arranged on the same axial line as the swiveling shaft, and the X-ray tube being axially supported on a spindle so as to enable a swiveling motion,
   the X-ray tube being supported on a proximal-end-side fixing plate and a distal-end-side fixing plate between the base unit and the display body so as to be sandwiched between both the plates, the proximal-end-side fixing plate having a proximal end supported around the axis of the swiveling shaft and swiveling with a swiveling motion of the swiveling shaft, the distal-end-side fixing plate having a distal end arranged around an axis of the spindle arranged on the base unit of the display body and swiveling with a swiveling motion of the swiveling shaft,
   a coupling shaft arranged in parallel with axial line of the swiveling shaft and the axial line of the spindle and penetrating the proximal-end-side fixing plate and the distal-end-side fixing plate to be axially supported by both the plates and used as the coupling body,
   a pinion meshing with a proximal-end-side gear fixed to the base unit and rotating on an axis with the coupling shaft rotating around the proximal-end-side gear with swiveling of the proximal-end-side fixing plate and the distal-end-side fixing plate with respect to the axial line of the swiveling shaft, and a pinion meshing with a distal-end-side gear fixed on the base unit of the display body and rotating on an axis with the coupling shaft rotating around the distal-end-side gear with swiveling of the proximal-end-side fixing plate and the distal-end-side fixing plate with respect to the axial line of the swiveling shaft and the axial line of the spindle being axially supported on the distal end of the coupling shaft.

4. The X-ray tube holding apparatus according to claim 3, wherein the proximal-end-side gear and the distal-end-side gear have a same outer diameter and a same tooth shape/number of teeth, central axes of the gears are set on a same axial line as the axial line of the swiveling shaft and the axial line of the spindle, and the pinions are formed with a same outer diameter and a same tooth shape/number of teeth.

5. The X-ray tube holding apparatus according to claim 3, wherein the display body includes an operation unit that enables an operator who is on the distal end of the X-ray tube with respect to the base unit to swivel the X-ray tube with respect to at least the base unit, translate the X-ray tube with respect to the ceiling or the floor surface, move up and down the X-ray tube with respect to the ceiling or the floor surface, or swivel the X-ray tube on the axial line of the vertical shaft.

* * * * *